(12) United States Patent
Kustra et al.

(10) Patent No.: US 12,156,699 B2
(45) Date of Patent: Dec. 3, 2024

(54) THERAPY PLANNING DEVICE

(71) Applicant: KONINKLIJKE PHILIPS N.V., Eindhoven (NL)

(72) Inventors: Jacek Lukasz Kustra, Eindhoven (NL); Aaldert Jan Elevelt, Best (NL); Teresa Nolte, Aachen (DE); Ralph Theodorus Hubertus Maessen, Roermond (NL); Zoi Tokoutsi, Eindhoven (NL); Volkmar Schulz, Wuerselen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 942 days.

(21) Appl. No.: 17/252,330

(22) PCT Filed: Jun. 18, 2019

(86) PCT No.: PCT/EP2019/065949
§ 371 (c)(1),
(2) Date: Dec. 15, 2020

(87) PCT Pub. No.: WO2019/243295
PCT Pub. Date: Dec. 26, 2019

(65) Prior Publication Data
US 2021/0259775 A1    Aug. 26, 2021

(30) Foreign Application Priority Data

Jun. 18, 2018 (EP) ..................................... 18178160

(51) Int. Cl.
*A61B 5/00* (2006.01)
*A61B 5/01* (2006.01)
(Continued)

(52) U.S. Cl.
CPC ................ *A61B 34/10* (2016.02); *A61B 5/01* (2013.01); *A61B 5/0537* (2013.01); *A61B 5/055* (2013.01);
(Continued)

(58) Field of Classification Search
CPC ......... A61B 34/10; A61B 5/01; A61B 5/0537; A61B 5/055; A61B 5/4872; A61B 5/4875;
(Continued)

(56) References Cited

U.S. PATENT DOCUMENTS 11,744,515 B2 * 9/2023 Rodriguez ........... A61B 5/4848
606/41
2014/0058387 A1 2/2014 Kruecker
(Continued)

FOREIGN PATENT DOCUMENTS

WO    WO2018092071 A1    5/2018

OTHER PUBLICATIONS

PCT International Search Report, International application No. PCT/EP2019/065949, Nov. 12, 2019.
(Continued)

*Primary Examiner* — Joel Lamprecht
(74) *Attorney, Agent, or Firm* — Sherry Austin

(57) ABSTRACT

The invention relates to a therapy planning device for planning a therapy to be applied to tissue of a subject (2). A tissue parameter distribution, which has been generated based on a magnetic resonance fingerprint scan of the tissue, and a therapy goal distribution, which defines a distribution of at least one parameter being indicative of a desired effect of the therapy, are provided. A machine learning module (13), which has been trained to output at least one therapy application parameter defining the application of the therapy based on an input tissue parameter distribution and an input
(Continued)

therapy goal distribution, is used for planning the therapy by determining the at least one therapy application parameter based on the provided tissue parameter distribution and the provided therapy goal distribution. This allows for a consideration of the actual quantitative tissue parameter distribution of the patient, thereby improving planning quality.

15 Claims, 5 Drawing Sheets

(51) Int. Cl.
```
A61B 5/0537      (2021.01)
A61B 5/055       (2006.01)
A61B 18/08       (2006.01)
A61B 34/10       (2016.01)
A61B 18/00       (2006.01)
```
(52) U.S. Cl.
CPC .......... *A61B 5/4872* (2013.01); *A61B 5/4875* (2013.01); *A61B 5/7267* (2013.01); *A61B 18/082* (2013.01); *A61B 2018/00577* (2013.01); *A61B 2034/101* (2016.02)

(58) Field of Classification Search
CPC .............. A61B 5/7267; A61B 18/082; A61B 2018/00577; A61B 2034/101; A61B 18/02; A61B 18/1492; A61B 90/37; A61B 2018/00529; A61B 2090/374; A61B 18/18; A61N 5/1039; A61N 7/022
See application file for complete search history.

(56) References Cited

U.S. PATENT DOCUMENTS

| | | |
|---|---|---|
| 2014/0296842 A1 | 10/2014 | Mansi |
| 2014/0378737 A1 | 12/2014 | Carpenter |
| 2016/0025835 A1 | 1/2016 | Gulani |
| 2016/0033604 A1 | 2/2016 | Grodzki |
| 2016/0059041 A1 | 3/2016 | Grodzki |
| 2016/0270687 A1 | 9/2016 | Brady-Kalnay |
| 2017/0106210 A1 | 4/2017 | Grodzki |
| 2017/0328973 A1 | 11/2017 | Amthor |
| 2020/0022649 A1* | 1/2020 | Rodriguez ........... A61B 5/4878 |

OTHER PUBLICATIONS

Schreurs T.J.L. et al., "Quantitative Multi-Parametric Magnetic Resonance Imaging of Tumor Response to Photodynamic Therapy", PLOS ONE | DOI:10.1371/journal.pone.0165759 Nov. 7, 2016, pp. 1-16.

Hectors S.J.C.G. et al., "MRI Methods for the Evaluation of High Intensity Focused Ultrasound Tumor Treatment: Current Status and Future Needs", Preclinical and Clinical Imaging Review, Magnetic Resonance in Medicine 75:302-317 (2016).

Ma D. et al., "Magnetic Resonance Fingerprinting", Nature, vol. 495, No. 7440, Mar. 13, 2013 (Mar. 13, 2013), pp. 187-192, XP055183037.

Hoppe E. et al., "Deep Learning for Magnetic Resonance Fingerprinting: A New Approach for Predicting Quantitative Parameter Values from Time Series", Studies in Health Technology and Informatics, 2017, 243, pp. 202-206.

Brace C. et al., "Thermal Tumor Ablation in Clinical Use", IEEE Pulse, vol. 2, No. 5, pp. 28-38, Sep.-Oct. 2011.

Yu H. et al., "Comparison of Percutaneous Ablation Technologies in the Treatment of Malignant Liver Tumors," Semin. Intervent. Radiol., vol. 31, No. 2, pp. 129-137, Jun. 2014.

Chu K. F. et al., "Thermal Ablation of Tumours: Biological Mechanisms and Advances in Therapy," Nature Review Cancer, vol. 14, No. 3, pp. 199-208, Feb. 2014.

Graham S.J. et al., "Analysis of Changes in MR Properties of Tissues After Heat Treatment, Magnetic Resonance in Medicine", 42(6):1061-71. 42:1061-1071 (1999).

Jiang et al., "MR Fingerprinting Using Fast Imaging with Steady State Precession (FISP) with Spiral Readout", Magnetic Resonance in Medicine 74:1621-1631 (2015).

Hand-Jorg R. et al., "Image-Based Monitoring of Magnetic Resonance-Guided Thermoablative Therapies for Liver Tumours", Cardiovascular and Interventional Radiology, (2012) vol. 35, No. 6.

* cited by examiner

THERAPY PLANNING DEVICE

CROSS-REFERENCE TO RELATED APPLICATIONS

This patent application claims the priority benefit under 35 U.S.C. § 371 of International Patent Application no. PCT/EP2019/065949, filed Jun. 18, 2019, which claims the benefit of European Patent Application No. EP18178160.0, filed on Jun. 18, 2018. These applications are hereby incorporated by reference herein in their entirety.

FIELD OF THE INVENTION

The invention relates to a therapy planning device, a therapy planning method and a computer program for planning a therapy to be applied to tissue of a subject. The invention relates further to a therapy system for applying a therapy to a subject, which includes the therapy planning device. Moreover, the invention relates to a training system, a training method and a computer program for training a machine learning module of the therapy planning device.

BACKGROUND OF THE INVENTION

A therapy, which needs to be planned, is, for instance, a thermal ablation therapy, wherein a tumor is ablated by energy in form of, for example, heat, cold or electricity and wherein a radiofrequency (RF) ablation device, a microwave ablation device or a cryo ablation device might be used, which is placed within or close to the tumor. For planning the ablation procedure therapy application parameters can be determined like the position of the ablation device and the settings of the ablation device, for instance, a voltage to be set at the ablation device, a duration of applying the energy, et cetera, wherein these therapy application parameters can be determined based on anatomical images of a patient showing the tumor and the surrounding of the tumor like a computed tomography (CT) image, a magnetic resonance (MR) image or an ultrasound image. For instance, in such an image the tumor can be delineated, in order to determine the dimensions and the position of the tumor within the patient, wherein this information can be used for planning the position of the ablation device, the settings of the ablation device and the duration of applying the energy such that the tumor is completely ablated and the surrounding of the tumor receives a minimal energy only or no energy at all from the ablation device. Although during therapy planning it is tried to determine the therapy application parameters such that only the tumor receives the energy, it can often not be prevented that also the surrounding tissue receives a significant part of the applied energy.

SUMMARY OF THE INVENTION

It is an object of the present invention to provide a therapy planning device, a therapy planning method and a computer program which allows for an improved planning of a therapy to be applied to tissue of a subject. It is a further object of the present invention to provide a therapy system for applying a therapy to a subject, which comprises the therapy planning device. Moreover, it is an object of the present invention to provide a training system, a training method and a computer program for training a machine learning module of the therapy planning device.

In a first aspect of the present invention a therapy planning device for planning a therapy to be applied to tissue of a subject is presented, wherein the therapy planning device comprises:
a tissue parameter distribution providing unit configured to provide at least one tissue parameter distribution which has been generated based on a magnetic resonance scan of the tissue,
a therapy goal distribution providing unit configured to provide at least one therapy goal distribution defining a distribution of at least one parameter being indicative of a desired effect of the therapy,
a machine learning module which has been trained to output at least one therapy application parameter defining the application of the therapy based on at least one input tissue parameter distribution and at least one input therapy goal distribution, and
a therapy planning unit configured to plan the therapy by determining the at least one therapy application parameter based on the provided at least one tissue parameter distribution, the provided at least one therapy goal distribution and the trained machine learning module.

According to embodiments of the invention, the tissue parameter distribution providing unit is configured to generate the at least one tissue parameter distribution based on a magnetic resonance fingerprint (MRF) scan. However, any other known magnetic resonance imaging scan or combination of magnetic resonance imaging scans could also be used for this purpose. According to preferred embodiments of the invention, at least one of the magnetic resonance imaging scans is a quantitative magnetic resonance imaging scan. The type of images resulting from the magnetic resonance imaging scans are preferably on or more of the following maps: electrical conductivity, thermal conductivity, water content, fat content, apparent diffusion coefficient (ADC) and MR relaxation time like a $T_1$ relaxation time or a $T_2$ relaxation time.

The remainder of this specification will be focused on MRF, but the person skilled in the art of MRI is aware that other types of (quantitative) magnetic resonance imaging scans may be used as an alternative.

When the at least one tissue parameter distribution has been generated based on an MRF scan of the tissue, the tissue parameter distribution is a quantitative distribution of a tissue parameter like the electrical conductivity, the thermal conductivity, the water content, the fat content, et cetera. Moreover, since the machine learning module has been trained to output at least one therapy application parameter like a position of an ablation device, settings of an ablation device or a duration of applying the therapy based on the at least one input tissue parameter distribution, i.e. based on a quantitative tissue parameter distribution, and at least one input therapy goal distribution, the therapy planning can consider the actual quantitative tissue parameter distribution of the patient, thereby improving the planning of the therapy.

The tissue parameter distribution providing unit is preferentially configured to determine the at least one tissue parameter distribution based on the MRF scan of the tissue. Moreover, the tissue parameter distribution providing unit is preferentially configured to provide as the at least one tissue parameter distribution a distribution of at least one of the following tissue parameters: electrical conductivity, thermal conductivity, water content, fat content, apparent diffusion coefficient (ADC) and MR relaxation time like a $T_1$ relaxation time or a $T_2$ relaxation time. The ADC is a tissue parameter which is indicative of the magnitude of diffusion of water within the tissue. It has been found that, if at least one of these specific tissue parameters is used, the therapy planning can be further improved.

Preferentially, the therapy planning device further comprises a) a therapy result distribution providing unit configured to provide at least one therapy result distribution defining at least one distribution of at least one parameter being indicative of at least one obtained effect of a therapy which has been applied in accordance with at least one therapy application parameter defining the applied therapy, and b) a training unit configured to train the machine learning module by using as training input at least the at least one provided tissue parameter distribution and the at least one provided therapy result distribution and as training output at least the at least one therapy application parameter according to which the therapy has been applied. Thus, a therapy result distribution can be used to further train the machine learning module. In particular, a therapy result distribution of a specific patient can be used for further training the machine learning module such that a personalized machine learning module can be generated.

It is preferred that the therapy result distribution providing unit is configured to provide the at least one therapy result distribution based on an MRF scan which has been carried out, after the therapy has been applied in accordance with the at least one therapy application parameter. Using an MRF scan for determining the therapy result distribution allows for a determination of the therapy result distribution based on quantitative tissue parameters. This allows for an improved provision of the therapy result distribution and hence to an improved training of the machine learning module. This improved training of the machine learning module can finally lead to a further improved planning of the therapy.

In an embodiment the therapy goal distribution providing unit is configured to provide as the at least one therapy goal distribution a distribution which defines that in a first region within the tissue the at least one parameter is larger than a predefined threshold and in another, second region within the tissue the at least one parameter is smaller than the predefined threshold. For instance, the first region can be a tumor region and the second region can be the region surrounding the tumor region, wherein the therapy goal distribution can be a distribution which defines that a tissue parameter should be larger than a predefined threshold in the tumor region and smaller than the predefined threshold in the region surrounding the tumor region. The therapy goal distribution can also define that in the tumor region a tissue parameter should be smaller than the predefined threshold and in the region surrounding the tumor region the tissue parameter should be larger than the predefined threshold. Thus, also the second region can be the tumor region and the first region can be the region surrounding the tumor region. The tissue parameter, which is used here, can be, for instance, the water content, the thermal conductivity, the electrical conductivity, an MR relaxation time like a $T_1$ relaxation time or a $T_2$ relaxation time, or an ADC. Moreover, in an embodiment the therapy goal distribution providing unit is configured to provide as the at least one therapy goal distribution a distribution of a tissue temperature obtained due to the therapy. For instance, a therapy goal distribution can define that in a tumor region the tissue temperature obtained due to the therapy should be larger than a predefined threshold and in a further region surrounding the tumor region the tissue temperature obtained due to the therapy should be smaller than the predefined temperature threshold. These therapy goal distributions allow for a very reliable definition of the desired therapy goal and hence for a further improved therapy planning which is based, inter alia, on the provided at least one therapy goal distribution.

The therapy planning device preferentially further comprises a therapy applicator characteristics providing unit for providing characteristics of a therapy applicator to be used for applying the therapy, wherein the machine learning module has been trained to output the at least one therapy application parameter defining the application of the therapy further based on characteristics of the therapy applicator, and wherein the therapy planning unit is configured to plan the therapy by determining the at least one therapy application parameter also based on the provided characteristics of the therapy applicator. The at least one therapy application parameter is, for instance, the shape of a therapy applicator, a relation between energy provided by the therapy applicator and settings of the therapy applicator like a set voltage of the therapy applicator, et cetera. By also considering the characteristics of the therapy applicator the planning of the therapy can be further improved.

In a further aspect of the present invention a therapy system for applying a therapy to a subject is presented, wherein the therapy system comprises:
  a therapy planning device for planning a therapy to be applied to tissue of the subject as defined by claim 1,
  a therapy applicator configured to apply the planned therapy to the subject.

In an embodiment the therapy system further comprises a) an MRF scanner for scanning the tissue while applying the planned therapy to the subject, b) a therapy result distribution providing unit configured to determine at least one therapy result distribution defining at least one distribution of at least one parameter being indicative of at least one obtained effect of the therapy which is applied in accordance with the planned therapy, wherein the at least one therapy result distribution is determined based on the scan carried out by the MRF scanner, and c) an output unit configured to provide an output being indicative of the determined at least one therapy result distribution. This allows a user like a radiologist to monitor the application of the therapy while applying the therapy such that the user can react, i.e., for instance, stop the application of the therapy, if the output indicates that this should be done.

In another aspect of the present invention a training system for training a machine learning module is presented, wherein the training system comprises:
  a therapy application parameter providing unit configured to provide at least one therapy application parameter defining an application of a therapy to tissue of a subject,
  a therapy result distribution providing unit configured to provide at least one therapy result distribution defining at least one distribution of at least one parameter being indicative of at least one obtained effect of the therapy which has been applied in accordance with the at least one therapy application parameter defining the applied therapy,
  a tissue parameter distribution providing unit configured to provide at least one tissue parameter distribution which has been generated based on an MRF scan of the tissue of the subject, before the therapy has been applied to the tissue,
  a training unit configured to train the machine learning module by using as training input at least the at least one provided tissue parameter distribution and the at least one provided therapy result distribution and as training output the at least one provided therapy application parameter.

In a further aspect of the present invention a therapy planning method for planning a therapy to be applied to tissue of a subject is presented, wherein the therapy planning method comprises:

providing at least one tissue parameter distribution, which has been generated based on an MRF scan of the tissue, by a tissue parameter distribution providing unit, providing at least one therapy goal distribution defining a distribution of at least one parameter being indicative of a desired effect of the therapy by a therapy goal distribution providing unit, providing a machine learning module which has been trained to output a therapy application parameter defining the application of the therapy based on at least one input tissue parameter distribution and at least one input therapy goal distribution, and planning the therapy by determining the at least one therapy application parameter based on the provided at least one tissue parameter distribution, the provided at least one therapy goal distribution and the trained machine learning module by a therapy planning unit.

In a further aspect of the present invention a training method for training a machine learning module is presented, wherein the training method comprises:

providing at least one therapy application parameter defining an application of a therapy to tissue of a subject by a therapy application parameter providing unit, providing at least one therapy result distribution defining at least one distribution of at least one parameter being indicative of at least one obtained effect of the therapy which has been applied in accordance with the at least one therapy application parameter defining the applied therapy by a therapy result distribution providing unit, providing at least one tissue parameter distribution which has been generated based on an MRF scan of the tissue of the subject, before the therapy has been applied to the tissue, by a tissue parameter distribution providing unit, training the machine learning module by using as training input at least the at least one provided tissue parameter distribution and the at least one provided therapy result distribution and as training output the at least one provided therapy application parameter by a training unit.

In another aspect of the present invention a computer program for planning a therapy to be applied to tissue of a subject is presented, wherein the computer program comprises program code means for causing a therapy planning device as defined in claim 1 to carry out the steps of the therapy planning method as defined in claim 12, when the computer program is run on a computer controlling the therapy planning device.

In a further aspect of the present invention a computer program for training a machine learning module is presented, wherein the computer program comprises program code means for causing a training system as defined in claim 11 to carry out the steps of the training method as defined in claim 13, when the computer program is run on a computer controlling the training system.

It shall be understood that the therapy planning device of claim 1, the therapy system of claim 9, the training system of claim 11, the therapy planning method of claim 12, the training method of claim 13, the computer program for planning a therapy of claim 14 and the computer program for training a machine learning module of claim 15, have similar and/or identical preferred embodiments, in particular, as defined in the dependent claims. It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
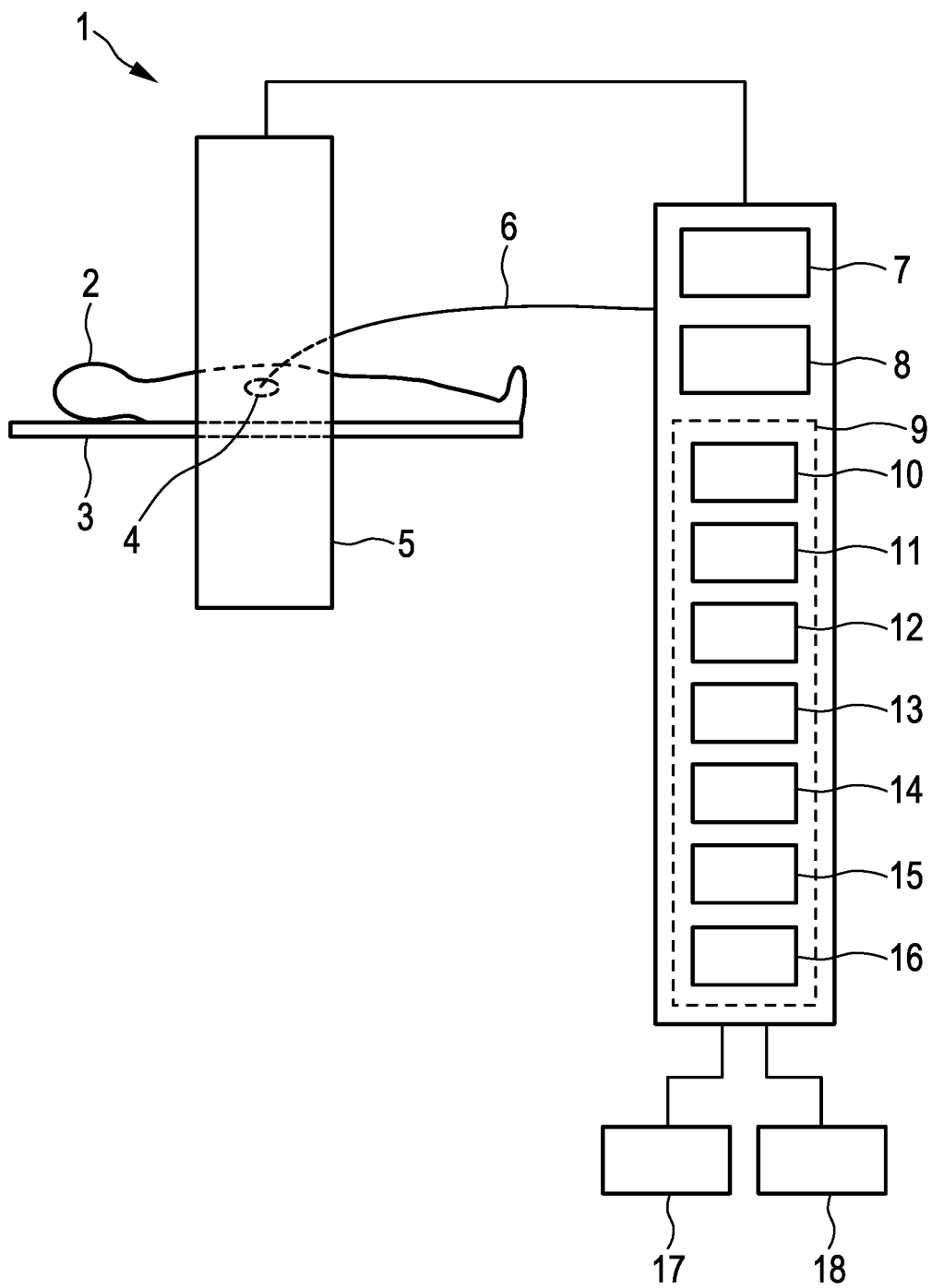
FIG. 1 shows schematically and exemplarily an embodiment of a therapy system for applying a therapy to a subject.

FIG. 1 shows schematically and exemplarily an embodiment of a therapy system for applying a therapy to a subject. The therapy system 1 comprises an MRF scanner 5 for generating MRF signals of a patient 2 lying on a support means 3 like a patient table. The MRF scanner is controlled by an MRF scanner control unit 7 which provides the MRF signals to a tissue parameter distribution providing unit 10. The tissue parameter distribution providing unit 10 is configured to determine at least one tissue parameter distribution based on the MRF signals received from the MRF scanner control unit 7.

MRF is known, especially MRF sequences are known, from, for instance, the articles "Magnetic resonance fingerprinting" by D. Ma et al., Nature, volume 495, pages 187-192 (2013) and "MR fingerprinting using fast imaging with steady state precession (FISP) with spiral readout" by Y. Jiang et al., Magnetic Resonance in Medicine, pages 1621-1631 (2015), which are herewith incorporated by reference. MRF can be based on a fast steady-state gradient echo sequence which can be both, spoiled and balanced. A fingerprinting sequence can comprise a series of consecutive RF pulses that are played out rapidly, using a randomized RF pulse strength, i.e. variable flip angles, and randomized timing, for instance, a randomized timing between consecutive pulses, i.e. a variable repetition time, or between a pulse and signal acquisition, i.e. variable echo times. The repetition times can be, for instance, in the range of 10 ms. Sensitivity to diffusion may be achieved by varying a spoiler gradient strength. The MRF signal acquisition can be fast due to the use of rapid k-space acquisition techniques such as spiral acquisition techniques or echo-planar imaging which may comprise undersampling. For each spatial position within the patient 2, i.e. in this embodiment, which refers to a three-dimensional case, for each voxel, a distinct signal evolution is measured which evolves according to the randomized sequence and the quantitative tissue parameters at the respective spatial position within the patient. Thus, for each spatial position within the patient a corresponding MRF signal is acquired by the MRF scanner 5.

For post processing, i.e. for determining the at least one tissue parameter distribution based on the MRF signals, the tissue parameter distribution providing unit 10 comprises a dictionary of many possible signal evolutions and assigned underlying tissue parameters. The quantitative parameter maps, i.e. the one or more tissue parameter distributions, are then obtained from the MRF signals by comparing the measured signal evolution in each voxel, i.e. by comparing the MRF signals, with the dictionary and by selecting the best matching signal evolution from the dictionary. This comparison with the dictionary yields one or several quantitative tissue parameters for each voxel. The tissue parameter distribution providing unit 10 can determine, for instance, a distribution of the electrical conductivity, of the thermal conductivity, of the water content, of the fat content, et cetera in a region within the patient including a tumor 4 and surrounding tissue of the patient. The tissue parameter distribution providing unit 10 could also be configured to determine, for instance, a distribution of an MR relaxation time and/or of an apparent diffusion coefficient in the region within the patient including the tumor 4 and surrounding tissue of the patient.

The tissue parameter distribution providing unit 10 can be regarded as being a component of a therapy planning device 9 for planning a therapy to be applied to tissue of the patient 2, wherein the therapy planning device 9 further comprises a therapy goal distribution providing unit 11 configured to provide at least one therapy goal distribution defining a distribution of at least one parameter being indicative of a desired effect of the therapy. For instance, the therapy goal distribution providing unit 11 can provide a therapy goal distribution defining a distribution of a desired water content, which should be present after the therapy has been applied to the tissue of the patient 2, wherein this therapy goal distribution can define that within a tumor region 4 the water content should be smaller than a predefined threshold and outside of the tumor region 4 the water content should be larger than the predefined threshold or larger than a further second predefined threshold. The therapy goal distribution providing unit 11 can also be configured to provide a desired temperature distribution as the therapy goal distribution, wherein the temperature distribution can define that the temperature within the tumor region 4 should be larger than a predefined temperature threshold while applying the therapy and the temperature outside of the tumor region 4 should be smaller than the temperature threshold.

The therapy planning device 9 further comprises a therapy applicator characteristics providing unit 12 for providing characteristics of a therapy applicator 6 to be used for applying the therapy. The provided characteristics are, for instance, the shape of the tip of the therapy applicator 6, a relation between energy applied by the therapy applicator 6 to the tissue of the patient 2 and settings of the therapy applicator 6 like a set voltage, et cetera. In this embodiment the therapy applicator is an RF ablation catheter with at least one ablation electrode for ablating tissue within the patient 2 by applying RF energy. The therapy system 1 comprises a therapy applicator control unit 8 for controlling the application of the therapy, i.e. for setting the voltage and/or the current and/or the frequency for the application of the ablation energy.

The therapy planning device 9 further comprises a machine learning module 13 which has been trained to output at least one therapy application parameter defining the application of the therapy based on at least one input tissue parameter distribution, at least one input therapy goal distribution and based on characteristics of the therapy applicator 6. The machine learning module 13 can be trained, for instance, to output a position of the tip of the ablation catheter 6 and settings to be set by the therapy applicator control unit 8. Furthermore, the therapy planning device 9 comprises a therapy planning unit 14 configured to plan the therapy by determining the at least one therapy application parameter based on the provided at least one tissue parameter distribution, the provided at least one therapy goal distribution and the provided characteristics of the therapy applicator 6 by using the machine learning module 13.

The therapy planning device 9 further comprises a therapy result distribution providing unit 15 configured to provide at least one therapy result distribution defining at least one distribution of at least one parameter being indicative of at least one obtained effect of a therapy which has been applied in accordance with at least one therapy application parameter defining the applied therapy. In particular, after a therapy has been applied to the patient 2, the MRF scanner 5 scans the patient 2, thereby generating MRF signals, wherein the therapy result distribution providing unit 15 is adapted to determine a distribution of tissue parameters as the therapy result distribution. The therapy result distribution providing unit 15 can also be adapted to, for instance, threshold a distribution of tissue parameters, in order to determine and then provide a therapy result distribution. For instance, to regions, in which the tissue parameter is larger than a predefined threshold, a first value like 0 can be assigned and to other regions, in which the tissue parameter is smaller than the predefined threshold, a second value can be assigned like 1, in order to determine and thereby provide the therapy result distribution. The therapy planning device 9 can further comprise a training unit 16 configured to train the machine learning module 13 by using as training input at least the at least one provided tissue parameter distribution which shows the situation before the therapy has been applied and the at least one provided therapy result distribution which shows the situation after the therapy has been applied, and as training output at least the at least one therapy application parameter according to which the therapy has been applied. This allows to further train the machine learning module 13.

The therapy result distribution providing unit 15 can also be configured to compare a distribution of tissue parameters, which has been determined after the therapy has been applied to the tissue, with a distribution of tissue parameters, which has been determined before the therapy has been applied to the tissue of the subject, in order to provide a therapy result distribution. For instance, the tissue parameter distribution showing the situation before the therapy has been applied and the tissue parameter distribution showing the situation after the therapy has been applied can be subtracted from each other, in order to provide the therapy result distribution. Also, the resulting difference distribution can be thresholded, in order to provide a therapy result distribution. This determination of the therapy result distribution can be carried out after the entire therapy has been applied to the tissue of the subject and/or after only a part of the therapy has been applied to the tissue of the subject. In particular, this determination of the therapy result distribution can be carried out while the therapy is applied to the tissue of the subject.

If the therapy result distribution providing unit 15 is configured to use a thresholding for determining the therapy result distribution, the corresponding threshold can be adjustable, in order to allow the threshold to be adapted to the respective patient. The threshold can be manually adjustable or automatically adjustable, wherein for an automatic adjustment of the threshold also machine learning can be used. It is also possible that the therapy result distribution providing unit includes assignments between tissue types and states of the respective tissue and thresholds, wherein for a specific patient the threshold is provided such that it corresponds to the type of tissue and the state of the respective tissue to be monitored. For instance, for different states of the liver like healthy liver, cirrhotic liver and fatty liver, different thresholds can be provided, wherein depending on the actual state of the liver of the patient, a respective threshold can be provided and used for the thresholding procedure.

The therapy system 1 further comprises an input unit 17 like a keyboard, a computer mouse, a touch pad, et cetera and an output unit 18 like a display. The output unit 18 can be adapted to provide an output being indicative of the at least one therapy result distribution provided by the therapy result distribution providing unit 15. In particular, the MRF scanner 5 can acquire MRF signals during the application of the therapy and the therapy result distribution providing unit 15 can be configured to determine the at least one therapy result distribution based on the acquired MRF signals in real-time, i.e. during the application of the therapy, thereby allowing a physician to monitor the application therapy in real-time and, for instance, to stop the application of the therapy, if required as indicated by the output real-time therapy result distribution.

Figure 2:
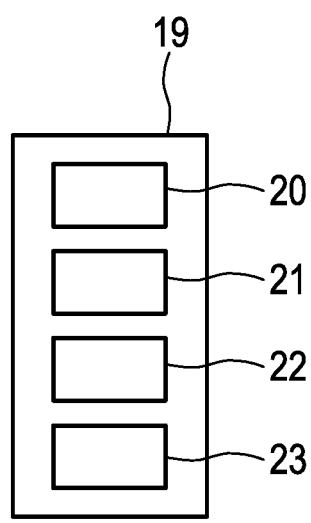
FIG. 2 shows schematically and exemplarily an embodiment of a training system for training a machine learning module.
Figure 3:
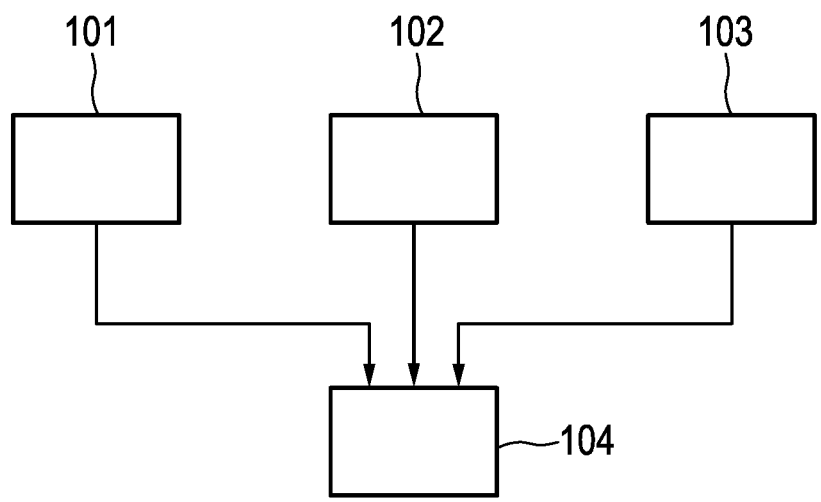
FIG. 3 shows a flowchart exemplarily illustrating an embodiment of a therapy planning method for planning a therapy to be applied to tissue of a subject.

FIG. 2 shows schematically and exemplarily an embodiment of a training system 19. The training system 19 comprises a therapy application parameter providing unit 20 configured to provide at least one therapy application parameter defining an application of a therapy to tissue of a subject. The training system 19 further comprises a therapy result distribution providing unit 21 configured to provide at least one therapy result distribution defining at least one distribution of at least one parameter being indicative of at least one obtained effect of the therapy which has been applied in accordance with the at least one therapy application parameter defining the applied therapy and a tissue parameter distribution providing unit 22 configured to provide at least one tissue parameter distribution which has been generated based on an MRF scan of the tissue of the subject, before the therapy has been applied to the tissue. Moreover, the training system 19 comprises a training unit 23 configured to train the machine learning module 13 by using, as training input, at least the at least one provided tissue parameter distribution and the at least one provided therapy result distribution and, as training output, the at least one provided therapy application parameter. In the following an embodiment of a therapy planning method for planning a therapy to be applied to tissue of a subject will exemplarily be described with reference to a flowchart shown in FIG. 3.

In step 101 at least one tissue parameter distribution like a distribution of water content is provided by the tissue parameter distribution providing unit 10, wherein the at least one tissue parameter distribution has been generated based on an MRF scan of the tissue carried out by the MRF scanner 5. Thus, at least one tissue parameter distribution is provided which is specific for the patient 2 within the MRF scanner 5. In step 102 at least one therapy goal distribution is provided, which defines a distribution of at least one parameter being indicative of a desired effect of the therapy, by the therapy goal distribution providing unit 11. For instance, the therapy goal distribution can define that within a tumor region 4 the water content should be smaller than a predefined threshold, after the therapy has been applied to the patient 2, and that in the region surrounding the tumor region 4 the water content should be larger than a further, second threshold.

In step 103 the machine learning module 13 is provided, which has been trained to output a therapy application parameter like a position of the ablation catheter 6 or settings of the ablation catheter 6 based on at least one input tissue parameter distribution like a distribution of the water content, before the therapy is applied to the patient 2, and at least one input therapy goal distribution like a water content distribution which should be present, after the therapy has been applied to the patient 2.

In step 104 the therapy is planned by the therapy planning unit 14 by determining the at least one therapy application parameter like the position of the ablation catheter 6 or the settings of the ablation catheter 6 based on the provided at least one tissue parameter distribution, the provided at least one therapy goal distribution and the trained machine learning module 13.

Figure 4:
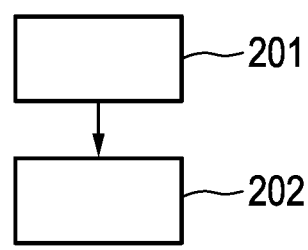
FIG. 4 shows a flowchart exemplarily illustrating an embodiment of a training method for training a machine learning module, and FIG. 5 schematically and exemplarily illustrates a therapy result distribution.

In the following an embodiment of a training method for training the machine learning module 13 will exemplarily be described with reference to a flowchart shown in FIG. 4.

In step 201 at least one therapy application parameter defining an application of a therapy to tissue of a subject is provided by a therapy application parameter providing unit 20. Moreover, in step 201 at least one therapy result distribution defining at least one distribution of at least one parameter being indicative of at least one obtained effect of the therapy is provided by the therapy result distribution providing unit 21, wherein the therapy result distribution has been applied in accordance with the at least one therapy application parameter defining the applied therapy. Furthermore, in step 201 at least one tissue parameter distribution is provided, which has been generated based on an MRF scan of the tissue of the subject, before the therapy has been applied to the tissue, by the tissue parameter distribution providing unit 22. In particular, in step 201 different training sets are provided, wherein each training set comprises at least one therapy application parameter, at least one therapy result distribution and at least one tissue parameter distribution. The training sets can each also comprise characteristics of a respective therapy applicator, wherein in step 202 these training sets are used for training the machine learning module 13 by the training unit 23. In particular, as training input at least the at least one provided tissue parameter distribution, the at least one provided therapy result distribution and preferentially also the characteristics of the respective therapy applicator are used, wherein the at least one provided therapy application parameter is used as training output.

The therapy planning device described above provides a data driven approach enabled by the quantitative nature of MRF scans, in order to learn optimal therapy parameters for a given patient, thereby providing personalized therapy planning. An initial MRF scan, i.e. an MRF scan, which has been carried out before applying the therapy, can be used to plan, for example, ablation settings, i.e. therapy application parameters. An MRF scan can then also be used to monitor the actual result of the applied therapy. This information can then be used to train the machine learning module, wherein this can be done for different patients, in order to improve the therapy planning.

The therapy applicator is preferentially configured to carry out a focal therapy for ablating a tumor by energy in form of, for instance, heat, cold or electricity. For instance, the therapy applicator can be an RF ablation device, a microwave ablation device or a cryo ablation device which might be configured to be introduced percutaneously and placed within the core of a tumor. Once the therapy applicator is positioned, the therapy applicator can be switched on to ablate the tumor. The position of the therapy applicator and the settings of the therapy applicator can be planned by using the therapy planning device as described above.

The therapy applicator is preferentially adapted to ablate the tissue such that proteins are coagulated which results in the extrusion of water from the tissue. Thus, in an embodiment the water content distribution is determined by using an MRF scan, wherein this distribution of the water content is used for providing a therapy result distribution, i.e. in order to assess the result of an applied therapy, for instance, whether the tissue in a tumor region has been ablated completely or not. Thus, MRF is used for identifying alterations and can also be used for determining the presence of specific tissue.

Figure 5:
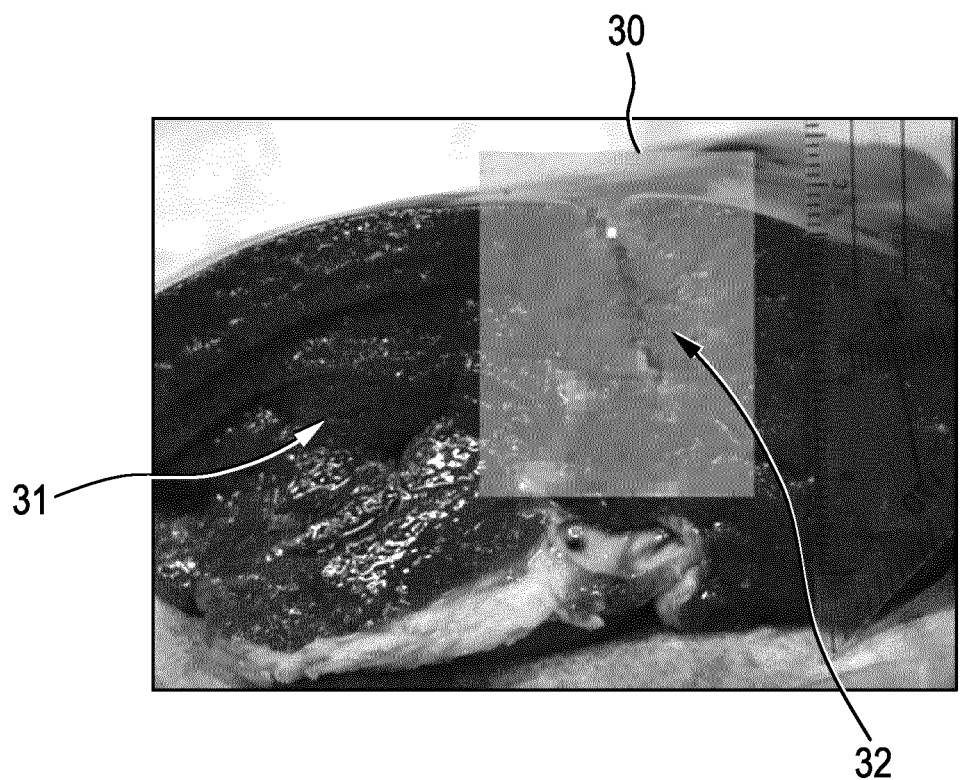

The therapy result distribution providing unit preferentially uses MRF to quantitatively validate the ablation results. Measuring one tissue parameter distribution or a number of tissue parameter distributions simultaneously on basis of which the viability of the tissue can be determined gives a very deep insight in the status of tissue. In particular, the MRF scanner can be adapted to simultaneously acquire different tissue parameter distributions in a relatively short scan time which is preferably smaller than 20 seconds. FIG. 5 schematically and exemplarily shows such a therapy result distribution 30 being indicative of the water content within a liver 31, after a part of the liver has been ablated. The part of the liver, which has actually been ablated, can easily be identified in this therapy result distribution by the region 32.

In known clinical practice therapy planning is performed based on clinical guidelines, typically resulting from clinical trials over a population. The input towards planning starts with imaging data like CT data, MR imaging (MRI) data or ultrasound imaging data, wherein the anatomical positions of target structures like tumors and of organs at risk are identified through a delineation procedure. From this point onwards, the original imaging data is mostly ignored, as only the identified geometry of the various structures is used. In contrast to this, the therapy planning device described above uses the quantitative nature of MRF such that the specific tissue properties can be identified before the intervention and used as input for the planning of the ablation settings, i.e. for the determination of the at least one therapy application parameter. Also the result of the ablation therapy, i.e. the effect of the ablation therapy on the tissue, can be quantitatively measured afterwards based on MRF. This allows for a data-driven system actively learning the effects of specific therapy application parameters on specific tissues. Thus, the above described therapy planning device does not only take the geometry into account, but the specific tissue parameters of the patient are used to compute a personalized treatment plan. The measured therapy outcomes are further fed into the learning system, i.e. into a further training of the machine learning module, in order to provide a self-evolving approach towards therapy delivery, especially towards thermal therapy delivery.

Using MRF for validation and preferentially also for real-time tracking of the thermal ablation procedure provides a direct quantitative insight with respect to the effect of the procedure on the cells of the tissue. Measuring tissue properties by using MRF, which have a direct relation with, for instance, cell death and/or viability of the cells, increases the confidence into the end result of ablation. The therapy result distribution providing unit 15 can be adapted to assess the therapy outcome using only one MR imaging sequence providing quantitative data, i.e. one MRF sequence, or using several MRF sequences.

The determination of the therapy result distribution based on MRF can be used, as mentioned above, in real-time and also in a post therapy setting. In case of a real-time application, a user can adjust the application of the therapy, i.e. the therapy delivery, during the actual application of the therapy based on the provided real-time therapy result distribution. Moreover, in case of a real-time monitoring of the application of the therapy the therapy applicator is preferentially an MR compatible device. In case of post therapy monitoring the therapy applicator can also be a non-MR-compatible device. An MR compatible device is, for instance, a cryo ablation device or a high intensity focused ultrasound (HIFU) ablation device built from materials being MR compatible.

The training unit is preferentially adapted to use the at least one provided tissue parameter distribution, which has been determined based on MRF signals acquired before the therapy has been applied, characteristics of the therapy applicator like heatmaps for the respective ablation device, at least one therapy application parameter according to which the therapy has been applied like a position of an ablation device and used settings of the ablation device and at least one therapy result distribution like a distribution of a tissue parameter determined by using an MRF scan for training the machine learning module. The trained machine learning module is then used to provide a personalized therapy planning, wherein the personalization refers to the use of one or several actual tissue parameter distributions of the actual patient, which have been determined based on corresponding MRF scans.

For monitoring the ablation therapy, the therapy result distribution providing unit determines at least one therapy result distribution defining at least one distribution of at least one parameter being indicative of at least one obtained effect of the applied therapy depending on an MRF scan. For instance, a tissue parameter distribution is determined based on an MRF scan and the determined tissue parameter distribution is thresholded such that regions of complete necrosis are distinguished from other regions of the tissue.

In an embodiment which allows for real-time therapy monitoring, after positioning the ablation device, i.e. the therapy applicator, in a target area like a tumor region, the patient stays in the MRF scanner during treatment. During the application of the therapy an MRF sequence is played out in regular intervals, wherein the matching to the dictionary of signal evolutions is immediately executed and the resulting parameter maps, i.e. the resulting tissue parameter distributions, are shown on the output unit 18. The output indicates to the user like a radiologist the different types of tissue identified on the basis of the tissue parameter distributions, wherein a delineation of the tissue damage is suggested to the radiologist based on the change of the tissue parameters with respect to a baseline, i.e. with respect to a tissue parameter distribution which has been determined before the therapy has been applied to the tissue. Based on that information the treatment progress can be judged and if needed manipulated, such as finishing the procedure or, if necessary, parameters of the ablation treatment may be adjusted by the user, i.e., for instance, the duration of the treatment, the target temperature of the treatment, ablation power input, position of the ablation device, et cetera can be modified.

In case of real-time monitoring, the therapy applicator, i.e. the ablation device, is MR compatible. If in an embodiment the ablation device is not MR compatible, treatment intervals, i.e. intervals of applying ablation energy, and MRF scanning could be interleaved, allowing for multiple therapy loops with intermediate assessment of the therapy outcome. Also a post treatment assessment is possible, wherein in this case, after the ablation therapy has been completed, the non-MR-compatible ablation device is removed and the patient is transferred to an MRF scanner, i.e. an MR imaging scanner being configured to carry out MRF scans. An MRF scan is then carried out and absolute tissue parameter values are determined, i.e. tissue parameter distributions are determined, and these distributions are used for determining the extent of the necrotic zone which can be distinguished from surrounding tissue in the determined tissue parameter distributions. The MRF scan can be improved by tuning specific parameters to the target anatomy. These parameters are, for instance, flip angles, the number of pulses, sequence timing like repetition time and echo time, et cetera. For specific patient tissue properties like liver cirrhosis or known tumor types these could be further tuned. Thus, the MRF scan settings can be different for different targets of the therapy. For instance, corresponding assignments between targets and parameters defining the MRF scans can be provided such that the MRF scan can be adapted to the respective target.

Although in the embodiment described above with reference to FIG. 1 the therapy system comprises an MRF scanner, in another embodiment the therapy system might not comprise an MRF scanner. In particular, for generating the tissue parameter distribution based on the MRF scan an MRF scan can be used, which has been carried out before the therapy is applied to the patient, wherein the MRF scanner 5 can be located, for instance, in another room, i.e. not in the room in which the therapy is applied. Moreover, also an assessment of the result of the therapy can be carried out at another location at which an MRF scanner is located.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the planning of the therapy, the training of the machine learning module, the provision of the therapy result distribution for monitoring the therapy, et cetera, performed by one or several units or devices can be performed by any other number of units or devices. These procedures and/or the control of the therapy planning device in accordance with the therapy planning method and/or the control of the training system in accordance with the training method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a therapy planning device for planning a therapy to be applied to tissue of a subject. A tissue parameter distribution, which has been generated based on a magnetic resonance fingerprint scan of the tissue, and a therapy goal distribution, which defines a distribution of at least one parameter being indicative of a desired effect of the therapy, are provided. A machine learning module, which has been trained to output at least one therapy application parameter defining the application of the therapy based on an input tissue parameter distribution and an input therapy goal distribution, is used for planning the therapy by determining the at least one therapy application parameter based on the provided tissue parameter distribution and the provided therapy goal distribution. This allows for a consideration of the actual quantitative tissue parameter distribution of the patient, thereby improving planning quality.

The invention claimed is:

1. A therapy planning device for planning a thermal ablation therapy to be applied to tissue of a subject, the therapy planning device comprising:
   a memory storing a program for therapy planning;
   a processor, wherein execution of the program by the processor causes the processor to:
      obtain at least one tissue parameter distribution generated based on a magnetic resonance (MR) scan of the tissue,
      obtain at least one therapy goal distribution defining a distribution of at least one parameter being indicative of a desired effect of the therapy,
      obtain at least one therapy application parameter defining the application of the therapy, the therapy application parameter corresponding to an applicator parameter, wherein the at least one therapy application parameter is output from a machine learning algorithm based on at least one input tissue parameter distribution and at least one input therapy goal distribution, and
      provide a thermal ablation therapy plan based on the at least one tissue parameter distribution, the provided at least one therapy goal distribution and the at least one therapy application parameter.

2. The therapy planning device as defined by claim 1, wherein the at least one tissue parameter distribution is based on a magnetic resonance fingerprint (MRF) scan of the tissue.

3. The therapy planning device as defined by claim 1, wherein the at least one tissue parameter distribution is a distribution of at least one of the following tissue parameters: electrical conductivity, thermal conductivity, water content, fat content, apparent diffusion coefficient (ADC) and MR relaxation time.

4. The therapy planning device as defined by claim 1, wherein execution of the program by the processor further causes the processor to:
   provide at least one therapy result distribution defining at least one distribution of at least one parameter being indicative of at least one obtained effect of a therapy which has been applied in accordance with at least one therapy application parameter defining the applied therapy, and
   train the machine learning algorithm by using as training input at least the at least one provided tissue parameter distribution and the at least one provided therapy result distribution and as training output at least the at least one therapy application parameter according to which the therapy has been applied.

5. The therapy planning device as defined by claim 4, wherein execution of the program by the processor further causes the processor to:
provide the at least one therapy result distribution based on an MRF scan, after the therapy has been applied in accordance with the at least one therapy application parameter.

6. The therapy planning device as defined by claim 1, wherein execution of the program by the processor further causes the processor to:
provide as the at least one therapy goal distribution a distribution wherein in a first region within the tissue the at least one parameter is larger than a threshold and in a second region within the tissue the at least one parameter is smaller than the threshold.

7. The therapy planning device as defined by claim 1, wherein execution of the program by the processor further causes the processor to:
provide as the at least one therapy goal distribution a distribution of a tissue temperature obtained due to the therapy.

8. The therapy planning device as defined by claim 1, wherein the execution of the program by the processor further causes the processor to:
provide characteristics of a therapy applicator, wherein the machine learning algorithm has been trained to output the at least one therapy application parameter defining the application of the therapy further based on characteristics of the therapy applicator, and
determine the at least one therapy application parameter also based on the provided characteristics of the therapy applicator.

9. A therapy system for applying a thermal ablation therapy to a subject, the therapy system comprising:
a therapy planning device as defined by claim 1, and
a thermal ablation therapy applicator.

10. The therapy system as defined by claim 9, wherein the therapy system further comprises:
a MR scanner for scanning the tissue while applying the planned therapy to the subject,
wherein execution of the program by the processor further causes the processor to:
determine at least one therapy result distribution defining at least one distribution of at least one parameter based on the scan by the MR scanner, wherein the at least one distribution indicates at least one obtained effect of the therapy,
provide an output that indicates the determined at least one therapy result distribution.

11. A training system for training a machine learning module, the training system comprising:
a therapy application parameter providing unit configured to provide at least one therapy application parameter defining an application of a thermal ablation therapy to tissue of a subject,
a therapy result distribution providing unit configured to provide at least one therapy result distribution defining at least one distribution of at least one parameter being indicative of at least one obtained effect of the thermal ablation therapy which has been applied in accordance with the at least one therapy application parameter defining the applied thermal ablation therapy,
a tissue parameter distribution providing unit configured to provide at least one tissue parameter distribution which has been generated based on an magnetic resonance scan of the tissue of the subject, before the thermal ablation therapy has been applied to the tissue,
a training unit configured to train the machine learning module by using as training input at least the at least one provided tissue parameter distribution and the at least one provided therapy result distribution and as training output the at least one provided therapy application parameter.

12. A therapy planning method for planning a thermal ablation therapy to be applied to tissue of a subject, the therapy planning method comprising:
obtaining at least one tissue parameter distribution generated based on a magnetic resonance (MR) scan of the tissue,
obtaining at least one therapy goal distribution, and
planning the therapy by determining at least one therapy application parameter using a machine learning algorithm, the therapy application parameter corresponding to an applicator parameter, wherein the output of the machine learning algorithm is based on the at least one tissue parameter distribution and the at least one therapy goal distribution.

13. A training method for training a machine learning module, the training method comprising:
providing at least one therapy application parameter defining an application of a thermal ablation therapy to tissue of a subject by a therapy application parameter providing unit,
providing at least one therapy result distribution defining at least one distribution of at least one parameter being indicative of at least one obtained effect of the thermal ablation therapy which has been applied in accordance with the at least one therapy application parameter defining the applied thermal ablation therapy by a therapy result distribution providing unit,
providing at least one tissue parameter distribution which has been generated based on an magnetic resonance scan of the tissue of the subject, before the thermal ablation therapy has been applied to the tissue, by a tissue parameter distribution providing unit,
training the machine learning module by using as training input at least the at least one provided tissue parameter distribution and the at least one provided therapy result distribution and as training output the at least one provided therapy application parameter by a training unit.

14. A non-transitory computer readable medium having stored thereon a computer program for planning a therapy to be applied to tissue of a subject, the computer program comprising instructions for causing a therapy planning device to carry out the steps of the therapy planning method as defined in claim 12.

15. A non-transitory computer readable medium having stored thereon a computer program for training a machine learning module, the computer program comprising instructions for causing a training system to carry out the steps of the training method as defined in claim 13, when the computer program is run on a computer controlling the training system.

* * * * *